(12) United States Patent
Matyas et al.

(10) Patent No.: US 9,149,897 B2
(45) Date of Patent: Oct. 6, 2015

(54) ASSEMBLY TOOL FOR USE IN ASSEMBLING ORTHOPAEDIC PROSTHETIC COMPONENTS

(71) Applicants: Aaron J. Matyas, Fort Wayne, IN (US);
Kyle D. Steffe, Warsaw, IN (US);
Rebecca L. Chaney, Warsaw, IN (US);
Alec A. Birkbeck, Leeds (GB)

(72) Inventors: Aaron J. Matyas, Fort Wayne, IN (US);
Kyle D. Steffe, Warsaw, IN (US);
Rebecca L. Chaney, Warsaw, IN (US);
Alec A. Birkbeck, Leeds (GB)

(73) Assignee: DePuy (Ireland) (IE)

( * ) Notice: Subject to any disclaimer, the term of this patent is extended or adjusted under 35 U.S.C. 154(b) by 229 days.

(21) Appl. No.: 13/828,914

(22) Filed: Mar. 14, 2013

(65) Prior Publication Data

US 2014/0259608 A1    Sep. 18, 2014

(51) Int. Cl.
*B23P 19/02* (2006.01)
*B23P 19/04* (2006.01)
*B23Q 1/00* (2006.01)
*B66F 1/08* (2006.01)
*B25B 5/08* (2006.01)
*A61F 2/46* (2006.01)
*B23P 19/027* (2006.01)
*B23P 19/10* (2006.01)
*B23Q 1/25* (2006.01)
*B23Q 5/34* (2006.01)
*B66F 3/28* (2006.01)
*B66F 9/22* (2006.01)
*A61F 2/38* (2006.01)
*A61F 2/30* (2006.01)

(52) U.S. Cl.
CPC .............. *B23P 19/04* (2013.01); *A61F 2/4637* (2013.01); *B23P 19/02* (2013.01); *B23Q 1/0018* (2013.01); *B25B 5/087* (2013.01); *B66F 1/08* (2013.01); *A61F 2/38* (2013.01); *A61F 2002/30332* (2013.01); *A61F 2002/30481* (2013.01); *A61F 2002/30558* (2013.01); *A61F 2002/30601* (2013.01); *A61F 2002/30738* (2013.01); *B23P 19/027* (2013.01); *B23P 19/10* (2013.01); *B23Q 1/25* (2013.01); *B23Q 5/348* (2013.01); *B66F 3/28* (2013.01); *B66F 9/22* (2013.01); *Y10T 29/49826* (2015.01); *Y10T 29/53* (2015.01); *Y10T 29/5383* (2015.01); *Y10T 29/53796* (2015.01); *Y10T 29/53909* (2015.01); *Y10T 29/53961* (2015.01); *Y10T 29/53978* (2015.01)

(58) Field of Classification Search
CPC .................. B23P 19/04; A61F 2/4637; A61F 2002/30332; A61F 2002/30558; A61F 2002/30738; A61F 2/38; A61F 2002/30601; A61F 2002/30481; Y10T 29/49826; Y10T 29/53; Y10T 29/53796; Y10T 29/53909; Y10T 29/53961; Y10T 29/53978; Y10T 29/53852; Y10T 29/53843; Y10T 29/53948; B25B 31/00; B25B 27/02; B25B 5/087; B23Q 1/0018; B23Q 1/25; B23Q 5/348; B66F 1/08; B66F 3/28; B66F 9/22
See application file for complete search history.

(56) References Cited

U.S. PATENT DOCUMENTS 5,800,546 A    9/1998  Marik et al.
6,238,435 B1   5/2001  Meulink et al.
(Continued)

OTHER PUBLICATIONS

European Search Report and Written Opinion, European Application No. 14157151.3-1654, Jul. 16, 2014, 5 pages.

*Primary Examiner* — Sarang Afzali
*Assistant Examiner* — Ruth G Hidalgo-Hernande
(74) *Attorney, Agent, or Firm* — Barnes & Thornburg LLP

(57) ABSTRACT

An assembly tool for use in assembling orthopaedic prosthetic components is disclosed. The assembly tool includes a frame, a base plate that includes a mounting bracket configured to engage a first end of an orthopaedic prosthetic component and a mechanical actuator configured to apply a compressive load to the orthopaedic prosthetic component.

16 Claims, 15 Drawing Sheets

(56) References Cited

U.S. PATENT DOCUMENTS

2002/0063245 A1* 5/2002 Salman .......................... 254/30
2004/0051030 A1* 3/2004 Olszak et al. .............. 250/208.1
2004/0054373 A1 3/2004 Serra et al.
2009/0281632 A1 11/2009 Naidu
2012/0291247 A1* 11/2012 Wang ........................... 29/281.1

* cited by examiner

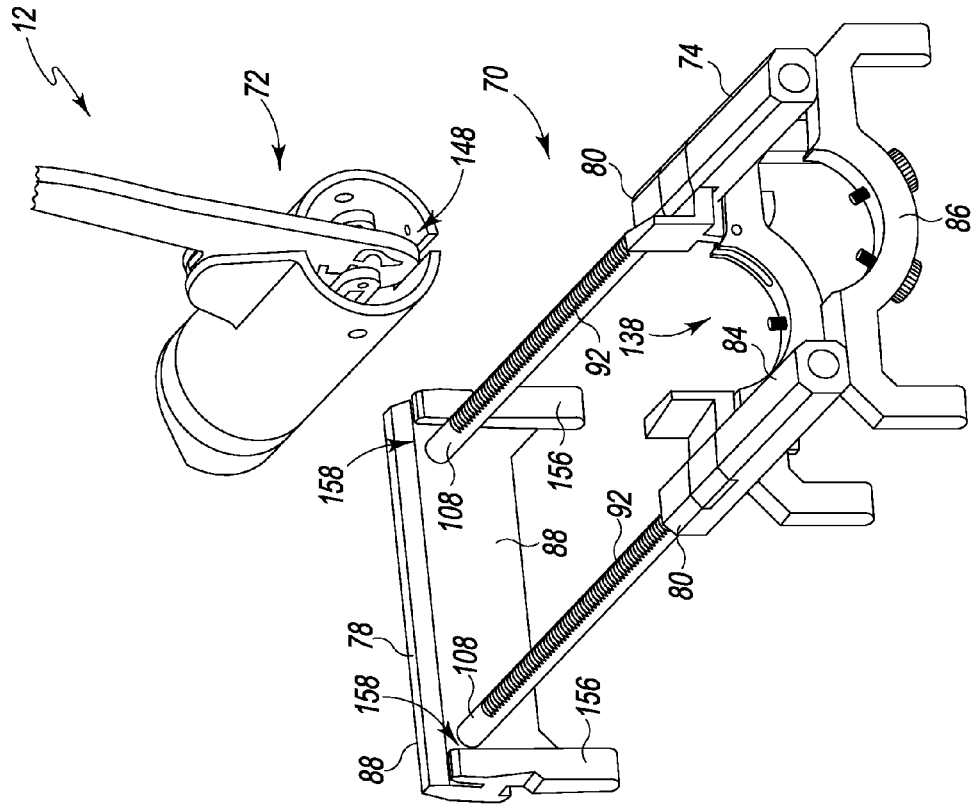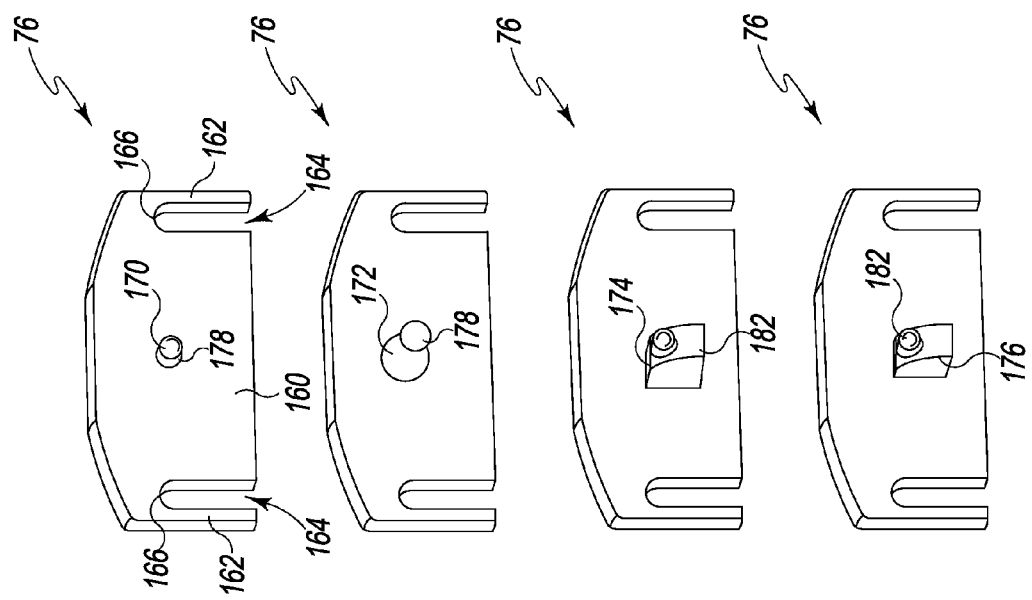
Fig. 3

ASSEMBLY TOOL FOR USE IN ASSEMBLING ORTHOPAEDIC PROSTHETIC COMPONENTS

TECHNICAL FIELD

The present disclosure relates generally to orthopaedic instruments for use in the performance of an orthopaedic joint replacement procedure, and more particularly to assembly tools used to assemble orthopaedic prosthetic components for implantation during an orthopaedic joint replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The tibial tray is configured to be coupled to surgically-prepared patient's tibia, and the femoral component is configured to be coupled to a surgically-prepared distal end of a patient's femur.

Such a knee prosthesis may also include a number of elongated intramedullary stem components which are implanted in the patient's tibia and/or femur. To secure a stem component to the patient's tibia and/or femur, the intramedullary canal of the patient's tibia and/or femur is first surgically prepared (e.g., reamed) such that the stem component may be subsequently implanted therein. In some designs, the stem component is implanted in the patient's bone by use of cementless fixation. One type of such a design is known as a "press fit" stem component.

SUMMARY

According to one aspect of the disclosure, an assembly tool for use in assembling orthopaedic prosthetic components includes a frame including a pair of telescopic rods, and a base plate secured to the telescopic rods. The base plate includes a mounting bracket configured to engage a first orthopaedic prosthetic component, and a mechanical actuator includes a housing secured to the frame. A ram plate configured to engage a second orthopaedic prosthetic component and a drive mechanism coupled to the ram plate.

The drive mechanism includes a connecting rod coupled to the ram plate, a handle rotatively coupled to the housing, and a clutch pin that may be moveable between an engaged position in which the handle may be coupled to the connecting rod such that rotation of the handle causes the ram plate to move toward the base plate and a disengaged position in which the handle may be decoupled from the connecting rod such that the ram plate remains stationary when the handle may be rotated. When the handle may be rotated from a first position to a second position, the handle engages an end of the clutch pin to move the clutch pin from the engaged position to the disengaged position.

In some embodiments, each telescopic rod may include a first shaft moveably coupled to a second shaft. The first shaft may include a plurality of teeth, and the frame may include a locking plate including a plurality of teeth configured to engage the teeth of the first shaft. The locking plate being moveable between a locked position in which the teeth of the locking plate are interdigitated with the teeth of the first shaft to prevent the first shaft from moving relative to the second shaft and an unlocked position in which the teeth of the locking plate are spaced apart from the teeth of the second shaft such that the first shaft may be permitted to move relative to the second shaft.

In some embodiments, the housing of the mechanical actuator may be removably coupled to the frame.

In some embodiments, the ram plate may be configured to move along a first axis toward the base plate when the handle may be rotated, and the clutch pin may be configured to move along a second axis between the engaged position and the disengaged position. The second axis extending orthogonal to the first axis.

In some embodiments, the connecting rod may have a slot defined therein. The clutch pin may include a cross beam that may be received in the slot when the clutch pin may be in the engaged position and spaced apart from the slot when the clutch pin may be in the disengaged position.

In some embodiments, the drive mechanism may include a guide body positioned in the housing. The guide body may include an aperture extending along the first axis, a guide slot extending along the second axis, and a link arm connecting the guide body and the handle. A connecting rod extends outwardly from the aperture to an end coupled to the ram plate and the cross beam of the clutch pin which may be moveable along the guide slot between the engaged position and the disengaged position.

In some embodiments, the link arm may be coupled to the handle via a joint. The joint may include a curved track defined in the handle and a cylindrical pin positioned in the curved track. The cylindrical pin may be configured to move along the curved track when the handle may be moved between the first position and the second position.

In some embodiments the assembly tool may include a locking mechanism coupled to the connecting rod, the locking mechanism being configured to prevent rotation of the handle.

In some embodiments, the locking mechanism may include a link having a first end moveably coupled to the connecting rod, and a pin secured to a second end of the link. The link may be moveable between a locked position in which the pin may be received in a notch defined in the handle such that rotation of the handle may be prevented, and an unlocked position in which the pin may be spaced apart from the notch such that rotation of the handle may be permitted.

In some embodiments, the link may have a slot defined therein and the cross beam of the clutch pin may be received in the slot of the link when the clutch pin may be in the engaged position and spaced apart from the slot of the link when the clutch pin may be in the disengaged position.

In some embodiments, the link may be moved to the unlocked position when a predetermined amount of force may be applied to the ram plate in a direction away from the base plate.

According to another aspect of the disclosure, an assembly tool for use in assembling orthopaedic prosthetic components includes a frame and a base plate coupled to the frame. The base plate includes a mounting bracket configured to engage a first orthopaedic prosthetic component, and a mechanical actuator including a housing secured to the frame, a ram plate configured to engage a second orthopaedic prosthetic component, and a drive mechanism coupled to the ram plate. The drive mechanism includes a handle rotatively coupled to the housing, the handle being operable to move the ram plate toward the base plate, and a locking mechanism configured to prevent rotation of the handle, the locking mechanism including a linkage coupled to the ram plate and a pin, the linkage being moveable between a locked position in which the pin may be received in a notch defined in the handle such that rotation of the handle may be prevented, and an unlocked position in which the pin may be spaced apart from the notch such that rotation of the handle may be permitted. Additionally, the linkage may be moved to the unlocked position when a predetermined amount of force may be applied to the ram plate in a direction away from the base plate.

In some embodiments, the drive mechanism may include a clutch pin that may be moveable between an engaged position in which the handle may be coupled to the ram plate such that rotation of the handle causes the ram plate to move toward the base plate and a disengaged position in which the handle may be decoupled from the ram plate such that the ram plate remains stationary when the handle may be rotated. The handle may be configured to engage the clutch pin during rotation to move the clutch pin from the engaged position to the disengaged position.

In some embodiments, the linkage may have a slot defined therein, and the clutch pin may include a cross beam that may be received in the slot of the linkage when the clutch pin may be in the engaged position and spaced apart from the slot of the linkage when the clutch pin may be in the disengaged position.

In some embodiments the assembly tool clutch pin may be biased in the engaged position.

In some embodiments, the assembly tool may include a plurality of base plates configured to be coupled to the frame, each base plate including a mounting bracket configured to engage a different orthopaedic prosthetic component.

According to one aspect of the disclosure, a method of assembling orthopaedic prosthetic components includes selecting a first prosthetic component having a tapered post and inserting the tapered post into a tapered bore of a second prosthetic component. Positioning the first prosthetic component and the second prosthetic component between a ram plate and a base plate of an assembly tool, and moving the base plate in a first direction to a first position in which the base plate may be engaged the second prosthetic component. The first prosthetic component may be engaged with the ram plate and advancing the base plate in the first direction to a second position to unlock a handle of the assembly tool, locking the base plate in the second position, and operating the handle to move the ram plate in a second direction opposite the first direction to secure the first prosthetic component to the second prosthetic component.

In some embodiments the method may include selecting a base plate from a plurality of base plates. Each base plate including a mounting bracket configured may be secured to a different second orthopaedic prosthetic component and securing the base plate to a frame of the assembly tool.

In some embodiments, operating the handle may include rotating the handle toward the ram plate to a first position in which a clutch pin may be permitted to engage a connecting rod to couple the handle to the ram plate. Continuing to rotate the handle to move the ram plate in the second direction, and rotating the handle to a second position to disengage the clutch pin from the connecting rod such that the handle may be decoupled from the ram plate.

In some embodiments, advancing the base plate in the first direction to the second position to unlock the handle of the assembly tool may include moving the ram plate in the first direction to withdraw a pin from a notch defined in the handle.

BRIEF DESCRIPTION OF THE DRAWINGS

The detailed description particularly refers to the following figures, in which:

FIG. 3 is an exploded perspective view of the assembly tool of FIG. 1;

FIG. 4A is another perspective view of the frame of the assembly tool of FIG. 1;

DETAILED DESCRIPTION OF THE DRAWINGS

Figure 1:
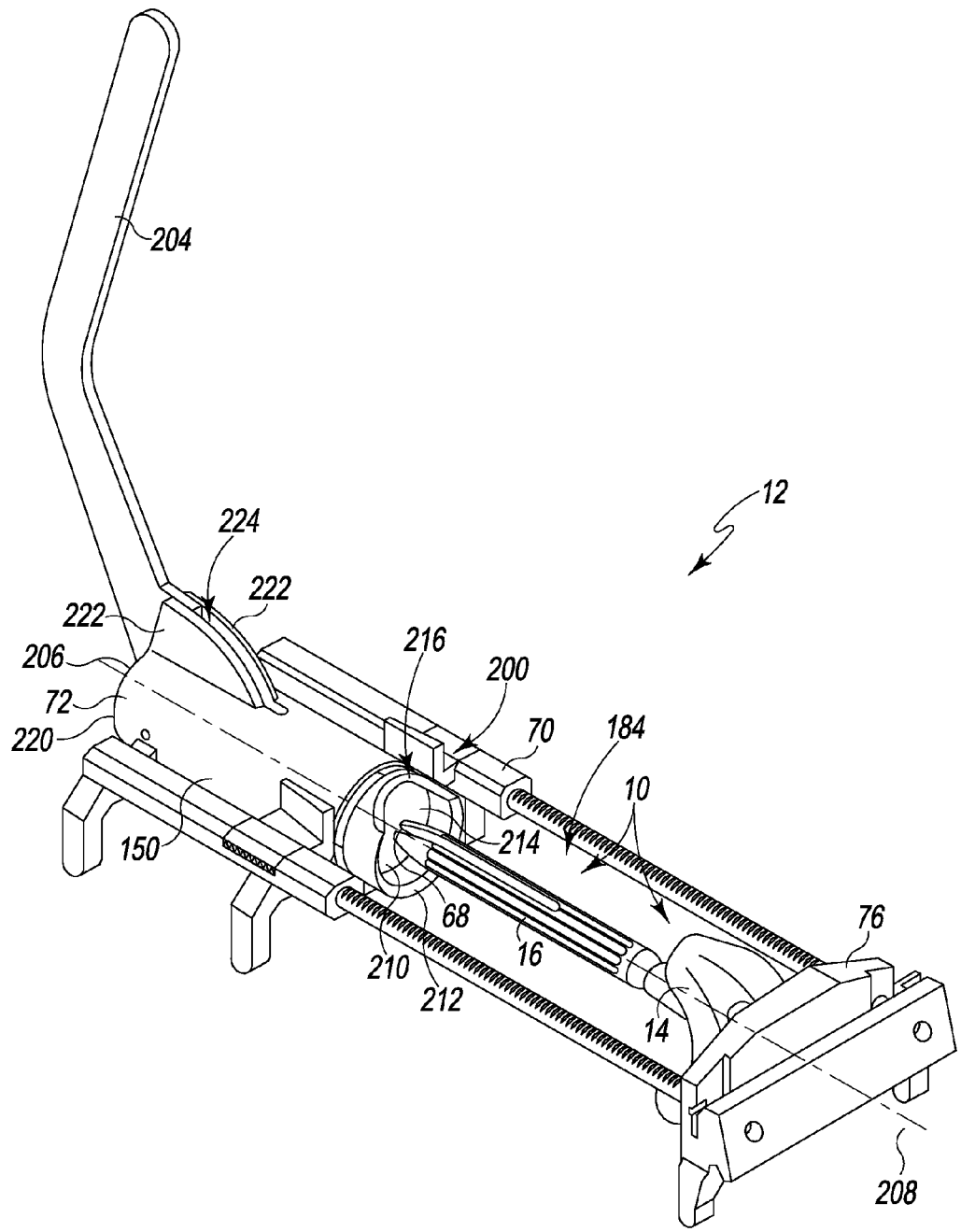
FIG. 1 is a perspective view of a number of orthopaedic prosthetic components and an assembly tool for use in assembling the orthopaedic prosthetic components.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, a number of orthopaedic prosthetic components 10 are shown positioned in an assembly tool 12. The orthopaedic prosthetic components 10 may be used in the performance of an orthopaedic knee replacement procedure. The components 10 includes a femoral component 14 configured to be secured to a stem component 16 via an interference fit. As described in greater detail below, the assembly tool 12 is configured to apply a compressive load to the components 14, 16 to secure the femoral component 14 to the stem component 16.

Figure 2:
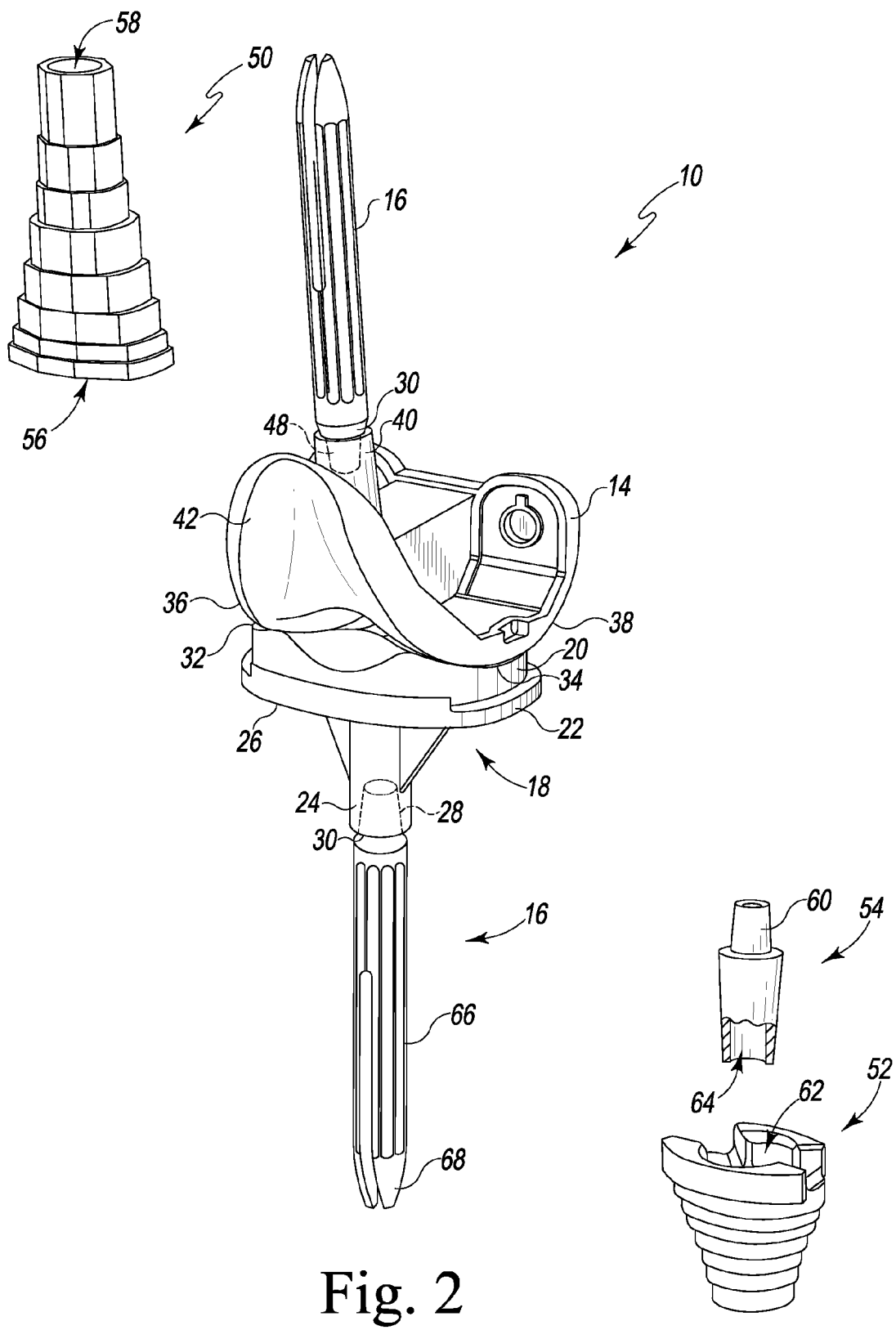
FIG. 2 is an exploded perspective view of an orthopaedic knee prosthesis.

The assembly tool 12 may also be used to assemble other prosthetic components 10, which are shown in FIG. 2. The prosthetic components 10 include a tibial tray 18 and a tibial bearing 20 configured to be positioned between the tibial tray 18 and the femoral component 14. The tibial tray 18 is configured to be implanted into a surgically-prepared end of a patient's proximal tibia (not shown). The tibial tray 18 includes a platform 22 having an elongated stem post 24 extending inferiorly away from its inferior surface 26. The elongated tibial stem post 24 is configured to receive a stem component 16, as described in greater detail.

The components 10 may include a number of stem components 16, and each of the variously-sized stem components 16 may be secured to either the tibial tray 18 or the femoral component 14. Specifically, as shown in FIG. 2, the stem post 24 of the tibial tray 18 has a tapered bore 28 formed therein into which a tapered post 30 of the stem component 16 may be advanced to taper lock the post 30 (and hence the stem component 16) and the tibial tray 18 to one another. In that way, the stem component 16 is secured to the tibial tray 18 via a form of interference fit (i.e., a taper lock). The stem component 16 may then be implanted into a surgically-prepared (e.g., reamed or broached) intramedullary canal of the patient's tibia.

The bearing 20 includes a lateral bearing surface 32 and a medial bearing surface 34. The bearing surfaces 32, 34 are configured to articulate with a lateral condyle surface 36 and a medial condyle surface 38, respectively, of the femoral component 14. Specifically, the femoral component 14 is configured to be implanted into a surgically-prepared distal end of the patient's femur (not shown), and is configured to emulate the configuration of the patient's natural femoral condyles. As such, the lateral condyle surface 36 and the medial condyle surface 38 are configured (e.g., curved) in a manner which mimics the condyles of the natural femur. The lateral condyle surface 36 and the medial condyle surface 38 are spaced apart from one another thereby defining an intercondylar notch therebetween.

The condyle surfaces 36, 38 are formed in a bearing surface 42 of the femoral component 14. The femoral component 14 also includes an elongated stem post 40, extending superiorly away from its opposite backside surface 44. The elongated femoral stem post 40 is configured to receive the stem component 16. Specifically, as shown in FIG. 2, the femoral component 14 has a tapered bore 48 formed therein into which a tapered post 30 of a stem component 16 may be advanced to taper lock the post 30 (and hence the stem component 16) and the femoral component 14 to one another. In that way, the stem component 16 is secured to the femoral component 14 via a form of interference fit (i.e., a taper lock). The femoral component 14 may then be implanted into a surgically-prepared (e.g., reamed or broached) intramedullary canal of the patient's femur.

As shown in FIG. 2, the components 10 may also include a number of optional components such as a femoral sleeve component 50, a tibial sleeve component 52, and a sleeve adaptor 54. The sleeve components 50, 52 may be used facilitate implantation of the femoral component 14 and the tibial tray 18, respectively, in the presence of reduced bone quality in the patient's femur or tibia. The femoral sleeve component 50 is configured to be secured to the femoral component 14 so as to be positioned between the femoral component 14 and the stem component 16. In particular, the inferior end 56 of the femoral sleeve component 50 has a bore (not shown) formed therein that may be taper locked to the outer surface of the femoral component's stem post 40 to lock the sleeve component 50 to the femoral component 14. The opposite, superior end of the femoral sleeve component 50 is configured to receive the stem components 16. Specifically, the superior end of the femoral sleeve component 50 has a tapered bore 58 formed therein into which a tapered post 30 of one of the stem components 16 may be advanced to taper lock the post 30 (and hence the stem component 16) and the femoral sleeve component 50 to one another.

The tibial sleeve component 52 may be embodied in a similar manner in which a bore formed in its superior end is taper locked to the stem post 24 of the tibial tray 18, with its opposite, inferior end having a tapered bore formed therein into which a tapered post 30 of one of the stem components 16 may be advanced to taper lock the post 30 (and hence the stem component 16) and the tibial sleeve component 52 to one another.

Alternatively, as shown in FIG. 2, the tibial sleeve component 52 may be used in conjunction with the sleeve adaptor 54. In such an embodiment, the sleeve adaptor 54 is used to secure both the stem components 16 and the tibial sleeve component 52 to the tibial tray 18. In particular, the sleeve adaptor 54 includes a tapered post 60 that is identical in shape and size to the tapered post 30 of each of the stem components 16. As such, the tapered post 60 of the sleeve adaptor 54 may be advanced into the tapered bore 28 formed in the tibial tray's stem post 24 to taper lock the post 60 (and hence the sleeve adaptor 54) and the tibial tray 18 to one another.

The tibial sleeve component 52 is configured to be secured to the sleeve adaptor 54 so as to be positioned between the tibial tray 18 and the stem component 16. In particular, the tibial sleeve component 52 has a bore 62 formed therein that extends through its entire length and hence is open to both its superior end and its inferior end. The tibial sleeve component 52 may be advanced over the sleeve adaptor 54 such that the tapered sidewalls forming the bore 62 of the tibial sleeve component 52 engage to the tapered outer surface of the sleeve adaptor 54 to taper lock the sleeve component 52 to the sleeve adaptor 54 to one another. As shown in FIG. 2, the inferior end of the sleeve adaptor 54 is configured to receive the stem components 16. Specifically, the inferior end of the sleeve adaptor 54 has a tapered bore 64 formed therein into which a tapered post 30 of one of the stem components 16 may be advanced to taper lock the post 30 (and hence the stem component 16) and the sleeve adaptor 54 to one another.

As shown in FIG. 2, each of the stem components 16 includes an elongated, generally cylindrical stem body 66. The tapered post 30 is positioned at a proximal end of the elongated stem body 66. The elongated stem body 66 extends distally away from the tapered post 30 and terminates at a rounded end 68 that defines the inferior-most surface of the stem component 16 when it is secured to a tibial tray 18 or the superior-most surface of the stem component 16 when it is secured to a femoral component 14.

The components 10 that engage the natural bone, such as the femoral component 14, the tibial tray 18, the stem components 16, and the sleeve components 50, 52, along with the sleeve adaptor 54, may be formed from an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

Referring now to FIG. 3, the assembly tool 12 includes a frame 70, a mechanical actuator 72 that may be secured to one end 74 of the frame 70, a plurality of base or holding plates 76 that may be secured to the other end 78 of the frame 70. The frame 70, the mechanical actuator 72, and the holding plates 76 are formed from a metallic material such as, for example, cobalt, including cobalt alloys such as a cobalt chrome alloy, titanium, including titanium alloys such as a Ti6Al4V alloy, and stainless steel. In the illustrative embodiment, the frame 70 includes a pair of telescopic rods 80 that connect a number of support beams 84, 86, 88.

Figure 4:
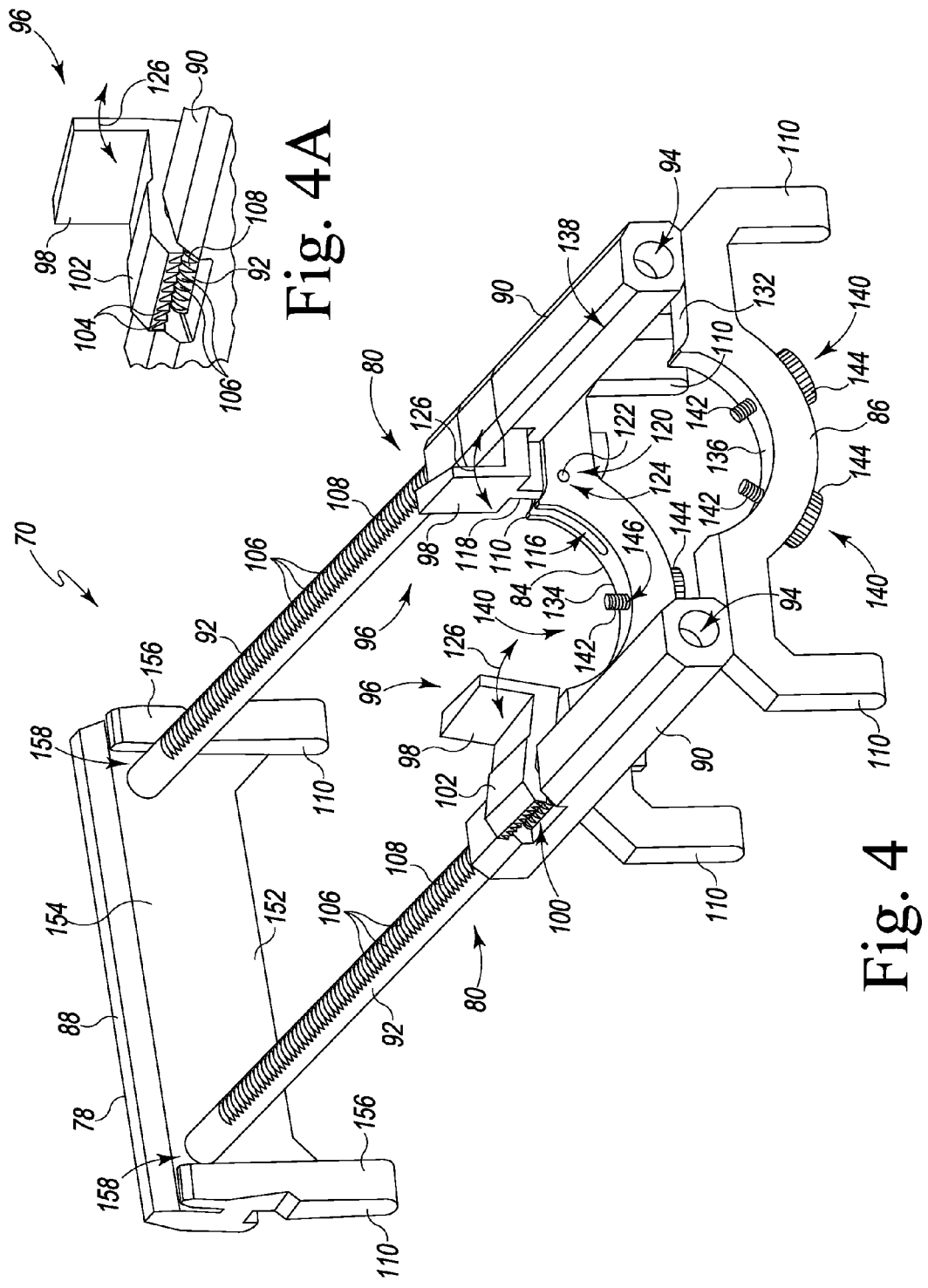
FIG. 4 is a perspective view of a frame of the assembly tool of FIG. 1.

As shown in FIG. 4, each telescopic rod 80 includes an outer shaft 90 secured to the support beams 84, 86 and an inner shaft 92 secured to the other support beam 88. The inner shaft 92 extends outwardly from, and telescopes into, a longitudinal passageway 94 extending through the outer shaft 90. In that way, the inner shaft 92 may be moved into and out of the outer shaft 90 to move the support beam 88 toward or away from the other beams 84, 86. Each telescopic rod 80 also includes a locking mechanism 96 configured to lock that rod's inner shaft 92 in position relative to the corresponding outer shaft 90.

In the illustrative embodiment, each locking mechanism 96 includes a user-operated button 98 configured to engage a corresponding inner shaft 92. As shown in FIG. 4, each outer shaft 90 has a groove 100 defined therein that opens into the passageway 94, and the user-operated button 98 includes a locking plate 102 sized to be positioned in groove 100. As shown in FIG. 4A, the locking plate 102 has a plurality of teeth 104 defined therein. The teeth 104 are configured to engage a plurality of teeth 106 defined in an upper surface 108 of the inner shaft 92 to prevent the inner shaft 92 from moving relative to the outer shaft 90. As described in greater detail below, each locking plate 102 is pivotally coupled to the support beam 84. In that way, the teeth 104 may be moved into and out of engagement with the teeth 106 of the inner shaft 92 such that the inner shaft 92 is selectively permitted to move relative to the outer shaft 90. It should be appreciated that in other embodiments the inner shaft may be configured to move relative to the support beam 88. In such embodiments, the frame 70 may include a locking mechanism to lock inner shaft relative to the support beam 88.

As shown in FIG. 4, the frame 70 includes a pair of mounting legs 110 that extend downwardly from the support beam 84. Each leg 110 is configured to support the assembly tool 12. The support beam 84 includes an upper surface 114 that supports the outer shafts 90 of the telescopic rods 80. A slot 116 is defined in the upper surface 114 adjacent to each outer shaft 90, and an arm 118 extends from each locking plate 102 into the slot 116. Each arm 118 is coupled to the support beam 84 via a joint 120. The joint 120 includes a pin 122 extending through bores 124 defined in the arm 118 and the support beam 84. The joint 120 permits the locking plate 102 to pivot as indicated by arrows 126 in FIGS. 4 and 4A between a locked position (see right user-operated button 98) in which the teeth 104, 106 are engaged such that the inner shaft 92 is prevented from moving relative to the outer shaft 90 and an unlocked position (see left user-operated button 98) in which the teeth 104, 106 are spaced apart such that movement of the inner shaft 92 is permitted. Each locking mechanism 96 also includes a biasing element such as, for example, a spring (not shown) to bias the locking plate 102 in the locked position.

The frame 70 includes another pair of mounting legs 110 that extend from the support beam 86. The support beam 86 includes an upper surface 132 that supports the outer shafts 90 of the telescopic rods 80. The beams 84, 86 include concave surfaces 134, 136, respectively, that cooperate to define a compartment 138 sized to receive the mechanical actuator 72.

In the illustrative embodiment, the assembly tool 12 includes a plurality of fasteners 140 configured to secure the mechanical actuator 72 to the frame 70. As shown in FIG. 4, each fastener 140 includes a threaded shaft 142 that extends from a knob 144. The fasteners 140 may be threaded into threaded holes 146 defined in the beams 84, 86 and threaded holes 148 defined in the housing 150 of the mechanical actuator 72.

As described above, the frame 70 also includes a support beam 88 that is secured to the inner shafts 92 at the end 78. The support beam 88 includes a pair of mounting legs 110 configured to support the assembly tool 12 and a bolster plate 152 extending between the mounting legs 110. As shown in FIG. 4, the inner shafts 92 extend outwardly from a planar surface 154 of the bolster plate 152, and the bolster plate 152 includes a pair of posts 156 that extend outwardly from the planar surface 154 on the outer side of each inner shaft 92. Each inner shaft 92 cooperates one of the posts 156 to define a slot 158 therebetween.

As described above, the assembly tool 12 also includes a plurality of base or holding plates 76 that may be secured to the end 78 of the frame 70. Each base plate 76 is configured to receive a different femoral component 14 or tibial tray 18. As shown in FIG. 3, each holding plate 76 includes a platform 160 and a pair of mounting arms 162. A channel 164 is defined between each mounting arm 162 and the platform 160. Each channel 164 is sized to receive one of the inner shafts 92 of the frame 70 and has a closed end 166.

To secure a holding plate 76 to the frame 70, the holding plate 76 is positioned above the support beam 88 such that the channels 164 are aligned with the inner shafts 92 of the frame 70. The holding plate 76 may then be moved downward to advance each mounting arm 162 of the holding plate 76 into the slot 158 defined between each inner shaft 92 and each post 156 of the frame 70. When the closed end 166 of the channel 164 engages the upper surface 108 of the inner shaft 92, the holding plate 76 is properly positioned on the frame 70.

As shown in FIG. 3, the holding plates 76 include mounting brackets 170, 172, 174, 176 having different configurations to support different prosthetic components. In the illustrative embodiment, each of the mounting brackets 170, 172, 174, 176 is configured to be used with a particular type of femoral component 14 or tibial tray 18. For example, the mounting bracket 170 includes a rounded alignment peg 178 configured to engage a fixed-bearing tibial tray while the mounting bracket 172 includes a cylindrical alignment peg 180 configured to engage a rotating platform tibial tray. Each of the mounting brackets 174, 176 includes a post 182 configured to engage a femoral component, with the mounting bracket 174 being angled relative to its platform 160 in one direction and the mounting bracket 176 being angled relative to its platform 160 in the opposite direction. In that way, the mounting brackets 174, 176 may be used with left and right femoral components, respectively. It should be appreciated that in other embodiments the assembly tool 12 may include additional plates 76 to support other prosthetic components.

As described above, the assembly tool 12 includes a mechanical actuator 72 that may be coupled to the frame 70. When the actuator 72 and one of the holding plates 76 are secured to the frame 70, the actuator 72 cooperates with holding plate 76 to define a chamber 184 into which the components 10 may be positioned for assembly. For example, as shown in FIG. 1, a femoral component 14 and a stem component 16 are positioned in the chamber 184 between the holding plate 76 and the actuator 72. As described in greater detail below, the actuator 72 is operable to apply a compressive load to the components 14, 16 to secure the femoral component 14 to the stem component 16.

The actuator 72 of the assembly tool 12 includes a housing 150 that is configured to be secured to the frame 70, a ram 200 positioned at one end 202 of the housing 150, and a handle 204 that extends outwardly from an opposite end 206 of the housing 150. As described in greater detail below, the handle 204 is operable to move the ram 200 relative to the housing 150 along an axis 208. The ram 200 includes a ram plate 210 and an annular wall 212 extending from a front surface 214 of the ram plate 210. As shown in FIG. 1, the annular wall 212 has a notch 216 defined therein, which is sized to receive the end 68 of the stem component 16 when the stem component 16 is positioned in the chamber 184.

Figure 5:
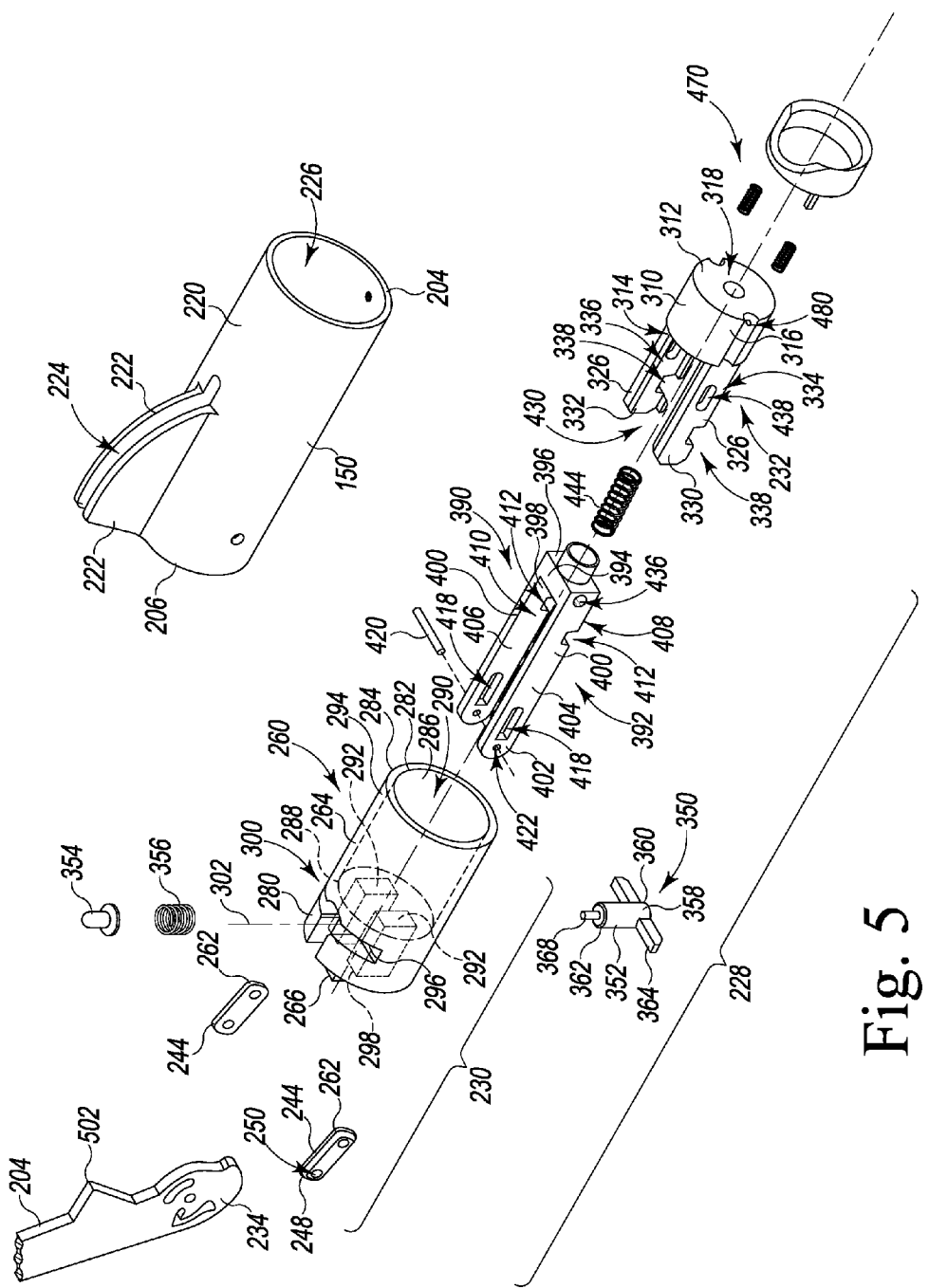
FIG. 5 is an exploded perspective view of a mechanical actuator of the assembly tool of FIG. 1.

The actuator housing 150 includes a cylindrical body 220 and a pair of flanges 222 that extend outwardly from the body 220 at the end 206. A guide slot 224 is defined between the flanges 222. As shown in FIG. 5, the guide slot 224 opens into a cylindrical passageway 226 extending through the ends 202, 206 of the housing 150. As described below, the cylindrical passageway 226 houses a number of components of the drive mechanism 228 of the actuator 72.

Figure 6:
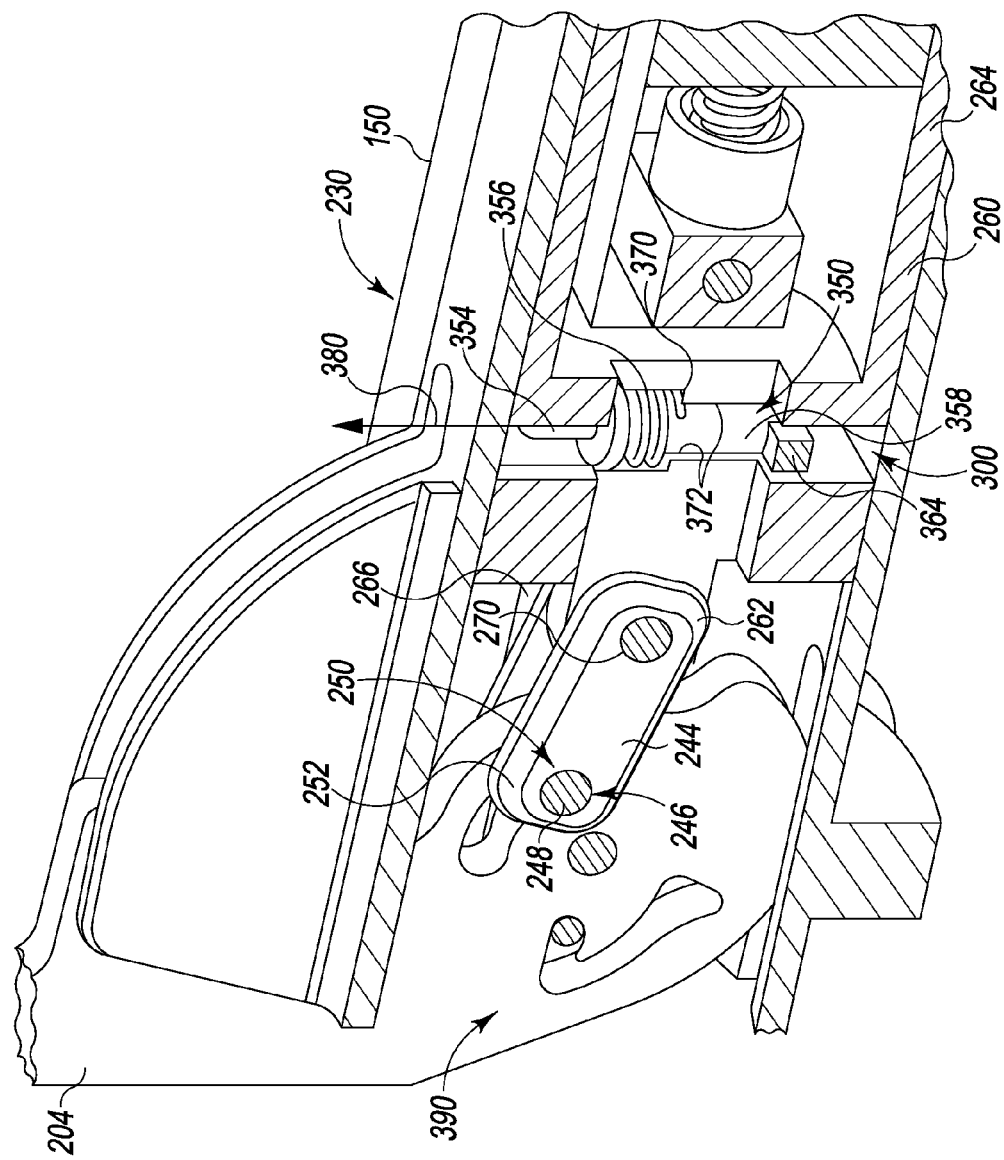
FIG. 6 is a fragmentary cross sectional perspective view of the mechanical actuator of FIG. 3.
Figure 7:
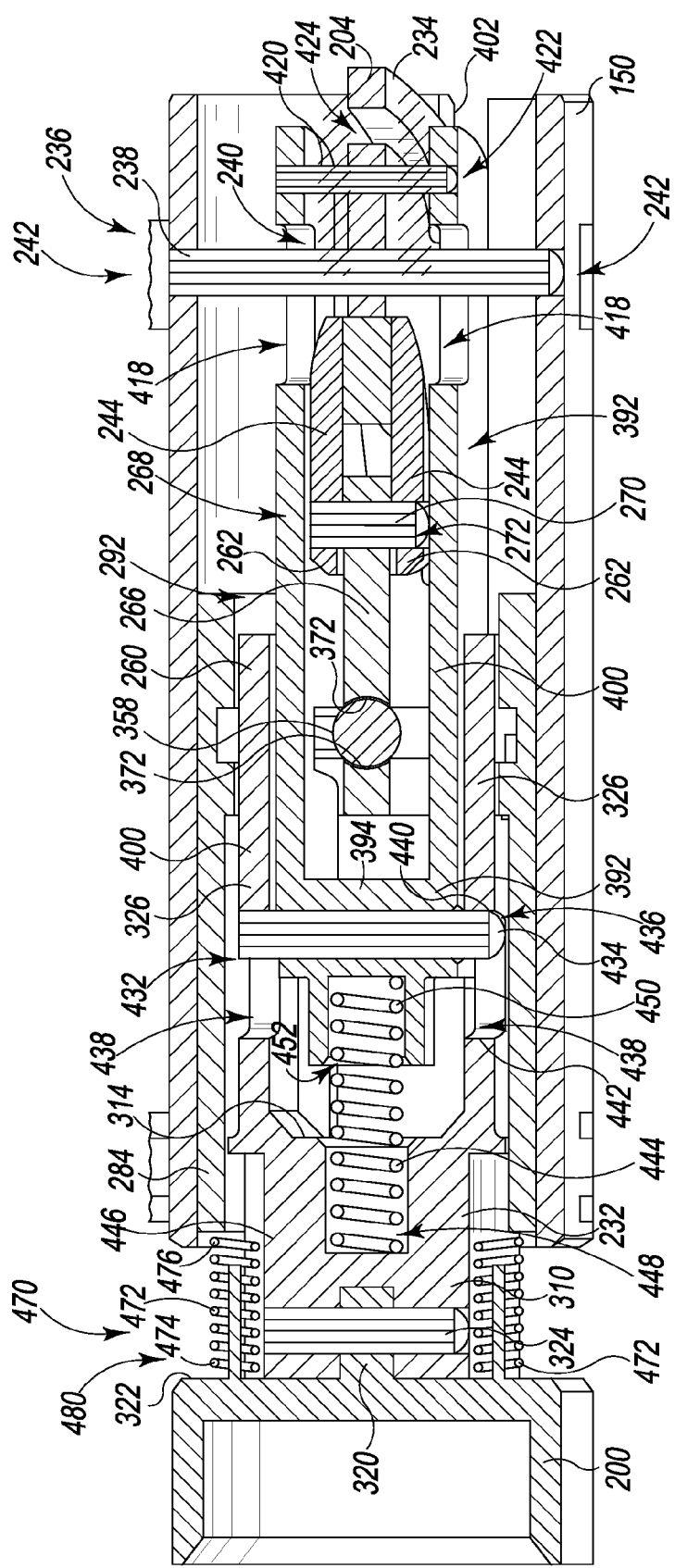
FIG. 7 is another fragmentary cross sectional perspective view of the mechanical actuator of FIG. 3.

Referring now to FIGS. 5-8, the drive mechanism 228 includes the handle 204, a connecting linkage 230 coupled to the handle 204, and a connecting rod 232 secured to the ram 200. The drive mechanism 228 also includes a clutch 350 configured to couple the connecting linkage 230 to the connecting rod 232 and hence couple the handle 204 to the ram 200, as described in greater detail below. In the illustrative embodiment, the handle 204 extends outwardly from the passageway 226 and the guide slot 224. The handle 204 includes a base 234 that is positioned in the passageway 226. As shown in FIG. 7, the handle base 234 is pivotally coupled to the housing 150 via a joint 236. The joint 236 includes a center pin 238 that extends through a bore 240 defined in the handle base 234 and a pair of bores 242 defined in the housing 150. As a result, the joint 236 permits the handle 204 to be rotated between a raised position (see FIG. 1) and a lowered position (see FIG. 14).

The connecting linkage 230 includes a pair of link arms 244 coupled to the handle base 234 via a joint 246. As shown in FIG. 6, the joint 246 includes a cylindrical pin 248 that is positioned in a bore 250 defined in an end 252 of each link arm 244. The cylindrical pin 248 extends through a curved track 254 that is defined in the handle base 234. As shown in FIG. 7, the track 254 defines an arc that extends from a lower end 256 to an upper end 258.

The connecting linkage 230 of the drive mechanism 228 also includes a guide body 260 coupled to the opposite ends 262 of the link arms 244. As shown in FIG. 6, the guide body 260 includes a shell 264 and a post 266 extending from the shell 264 toward the handle base 234. A joint 268 secures the post 266 to the ends 262 of the link arms 244. The joint 268 includes a cylindrical pin 270 that extends through bores 272 defined in the post 266 and the link arms 244. Thus, when the handle 204 is rotated, the link arms 244 are pivoted about the joints 246, 268 while the cylindrical pin 248 is moved between the ends 256, 258 of the track 254.

As shown in FIG. 5, the post 266 of the guide body 260 extends from an end 280 of the shell 264. The shell 264 has an opening 282 defined in the opposite end 284, and a cylindrical inner wall 286 extends inwardly from the opening 282 to a base wall 288. The walls 286, 288 cooperate to define an aperture 290 in the shell 264. The shell 264 also has a pair of rectangular passageways 292 that extend through the base wall 288 and out the end 280.

The shell 264 has a cylindrical outer surface 294 extending between the ends 280, 284 along the axis 208. In the illustrative embodiment, the diameter of the cylindrical outer surface 294 of the shell 264 is substantially matches the diameter of the passageway 226 of the housing 150. As a result, the shell 264 is constrained to move along the axis 208. A rectangular opening 296 is defined in the outer surface 294 and a number of inner walls 298 extend inwardly from the opening 296. As shown in FIG. 6, the inner walls 298 define a guide slot 300 extending through the entire shell 264 that is sized to receive the clutch 350. The guide slot 300 has a longitudinal axis 302 that extends orthogonal to the axis 208.

As described above, the drive mechanism 228 of the assembly tool 12 also includes a connecting rod 232 that is coupled to the ram 200. As shown in FIG. 5, the connecting rod 232 includes a head 310 having a front surface 312, a rear surface 314, and a cylindrical outer wall 316 extending between the surfaces 312, 314. An aperture 318 is defined in the center of the front surface 312, which is sized to receive a peg 320 extending from the rear surface 322 of the ram plate 210. A locking pin 324 (see FIG. 7) secures the ram 200 to the connecting rod 232.

The connecting rod 232 also includes a pair of elongated arms 326 that extend outwardly from the rear surface 314 of the head 310. Each arm 326 includes an outer surface 330, an inner surface 332, and a bottom wall 334 extending between the surfaces 330, 332. As shown in FIG. 5, an opening 336 is defined between the inner surfaces 332, and a groove 338 is defined in the bottom wall 334 of each arm 326.

As shown in FIG. 5, the drive mechanism 228 includes a clutch 350 configured to couple the connecting linkage 230 to the connecting rod 232 and hence couple the handle 204 to the ram 200. In the illustrative embodiment, the clutch 350 of the drive mechanism 228 includes a clutch pin 352 and a biasing element 356. The clutch pin 352 includes a body 358 extending from a lower end 360 to an upper end 362, and a stop cap 354 secured to the upper end 362. The cross beam 364 is secured to the lower end 360 of the body 358 and extends transverse to the longitudinal axis of the body 358. The body 358 also includes a peg 368 that extends upwardly form the upper end 362 of the body 358. The stop cap 354 is secured to the peg 368 of the body 358 via welding, an interference fit, or other fastening means.

Figure 8:
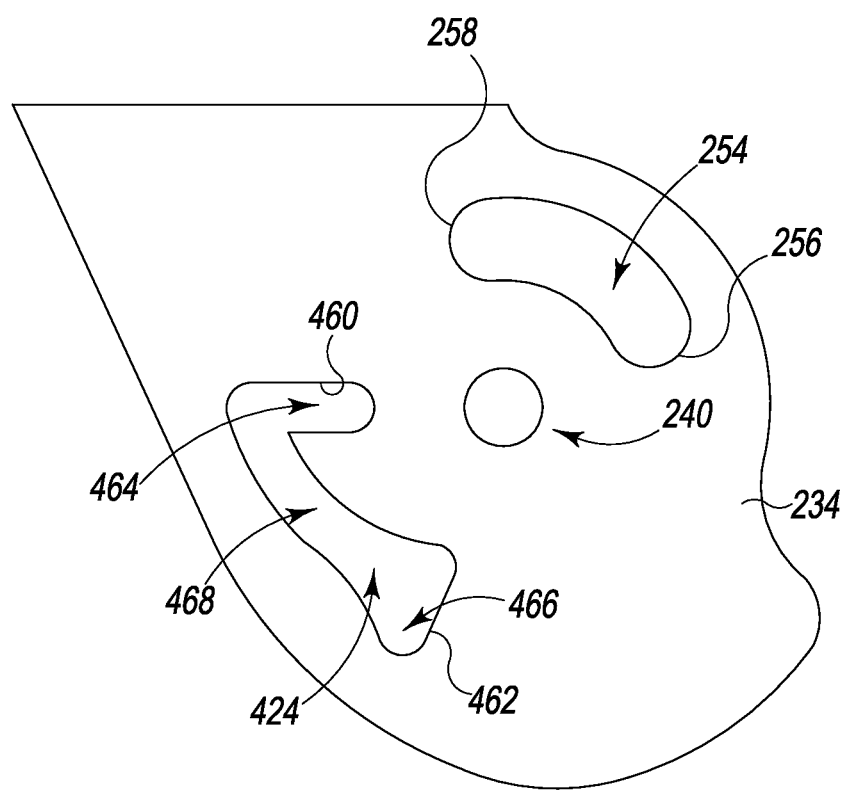
FIG. 8 is a fragmentary side elevation view of a handle of the mechanical actuator.

As described above, the guide body 260 includes a guide slot 300 defined by the inner walls 298, and, as shown in FIG. 6, the clutch 350 is positioned in the guide slot 300. The inner walls 298 of the guide body shell 264 define a shoulder 370 and a pair of curved surfaces 372 extending downwardly from the shoulder 370. As shown in FIG. 8, the curved surfaces 372 are shaped to match the diameter of the body 358 of the clutch pin 352 and thereby guide the movement of the clutch pin 352 along the axis 302 of the guide slot 300.

As shown in FIG. 6, the biasing element 356 of the clutch 350 is illustratively embodied as a spring. The spring 356 is positioned between the shoulder 370 and the stop cap 354. As such, the spring 356 exerts a bias on the clutch pin 352 in the upward direction indicated by arrow 380. In that way, the cross beam 364 is biased into engagement with the bottom walls 334 of the arms 326 of the connecting rod 232. As described in greater detail below, when the grooves 338 of the arms 326 are aligned with the cross beam 364, the cross beam 364 may be advanced into the grooves 338 to couple the guide body 260 to the connecting rod 232 such that rotation of the handle 204 causes movement of the ram 200.

The mechanical actuator 72 of the assembly tool 12 also includes a locking mechanism 390 that is configured to prevent rotation of the handle 204. As shown in FIG. 5, the locking mechanism 390 includes a link 392 configured to slide relative to the connecting rod 232 of the drive mechanism 228. The link 392 includes a body 394 having a front wall 396 and a rear wall 398. The link 392 also includes a pair of elongated arms 400 that extend away from the rear wall 398 to an end 402.

Each arm 400 of the link 392 includes an outer surface 404, an inner surface 406, and a bottom wall 408 extending between the surfaces 404, 406. An opening 410 is defined between the inner surfaces 406 of the arms 400. As shown in FIG. 8, the opening 410 is sized to receive the post 266 of the guide body 260. The arms 400 extend through the passageways 292 defined in the guide body 260 on each side of the post 266. Each arm 400 also has a groove 412 that is defined in its bottom wall 408. As described in greater detail below, the grooves 412 are sized to receive the cross beam 364 of the clutch 350.

Each arm 400 of the link 392 also has an elongated slot 418 extending through the inner surface 406 and the outer surface 404. As shown in FIG. 8, the center pin 238 of the joint 236 extends through the slots 418 as well as the bores 242 defined in the housing 150 and the bore 240 defined in the handle base 234. At the end 402 of the link 392, the locking mechanism 390 also includes a locking pin 420 that is positioned in a pair of bores 422 defined in the arms 400 and extends through a track 424 defined in the handle base 234, as described in greater detail below.

Returning to FIG. 5, each elongated arm 326 of the connecting rod 232 has a guide track 430 defined in its inner surface 332. Each guide track 430 is sized to receive one of the elongated arms 400 of the link 392. The link 392 is coupled to the connecting rod 232 via a joint 432. The joint 432 includes a cylindrical pin 434 that extends through a bore 436 defined in the body 394 of the link 392 and an elongated slot 438 defined in the each elongated arm 326 of the connecting rod 232. In that way, the cylindrical pin 434 is configured to move between the ends 440, 442 of the slot 438 such that the link 392 is permitted to slide relative to the connecting rod 232.

A biasing element, which is illustratively embodied as a spring 444, is positioned between the body 394 of the link 392 and the head 310 of the connecting rod 232. As shown in FIG. 7, the spring 444 has an end 446 positioned in an aperture 448 defined in the rear surface 314 of the head 310 and an end 450 positioned in an aperture 452 defined in the body 394 of the link 392. In the illustrative embodiment, the spring 444 biases the cylindrical pin 434 into engagement with the arms 326 at the end 440 of the slot 438.

As described above, a track 424 is defined in the handle base 234, and the locking mechanism 390 includes a locking pin 420 that extends through the track 424. As shown in FIG. 8, the track 424 extends from an upper end 460 to a lower end 462. A notch 464 defined at the upper end 460 of the track 424 and a pocket 466 defined at the lower end 462 of the track 424. A curved slot 468 connects the notch 464 to the pocket 466. When the locking pin 420 is positioned in the notch 464 as shown in FIG. 8, rotation of the handle 204 is prevented, as described in greater detail below.

As shown in FIG. 7, the locking mechanism 390 also includes a biasing element 470 that is positioned the ram plate 210 and the guide body shell 264. In the illustrative embodiment, the biasing element 470 includes a pair of springs 472, and each spring 472 has an end 474 that engages the rear surface 322 of the ram plate 210 and an end 476 that engages the end 284 of the guide body shell 264. Each spring 472 is positioned in a slot 480 defined in the cylindrical outer wall 316 of the head 310.

Figure 9:
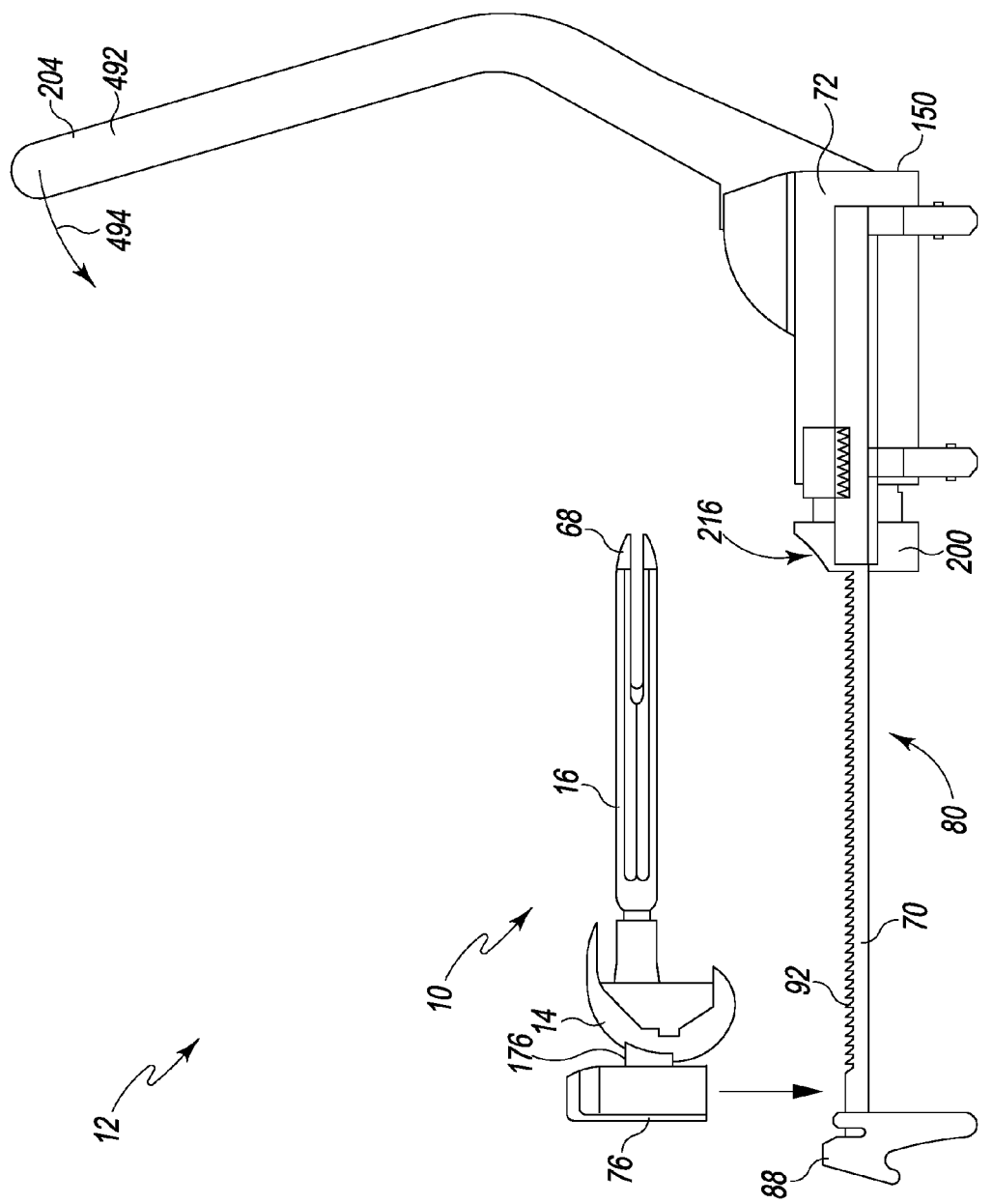
FIG. 9 is a side elevation view of the assembly tool and the orthopaedic prosthetic components of FIG. 1.
Figure 10:
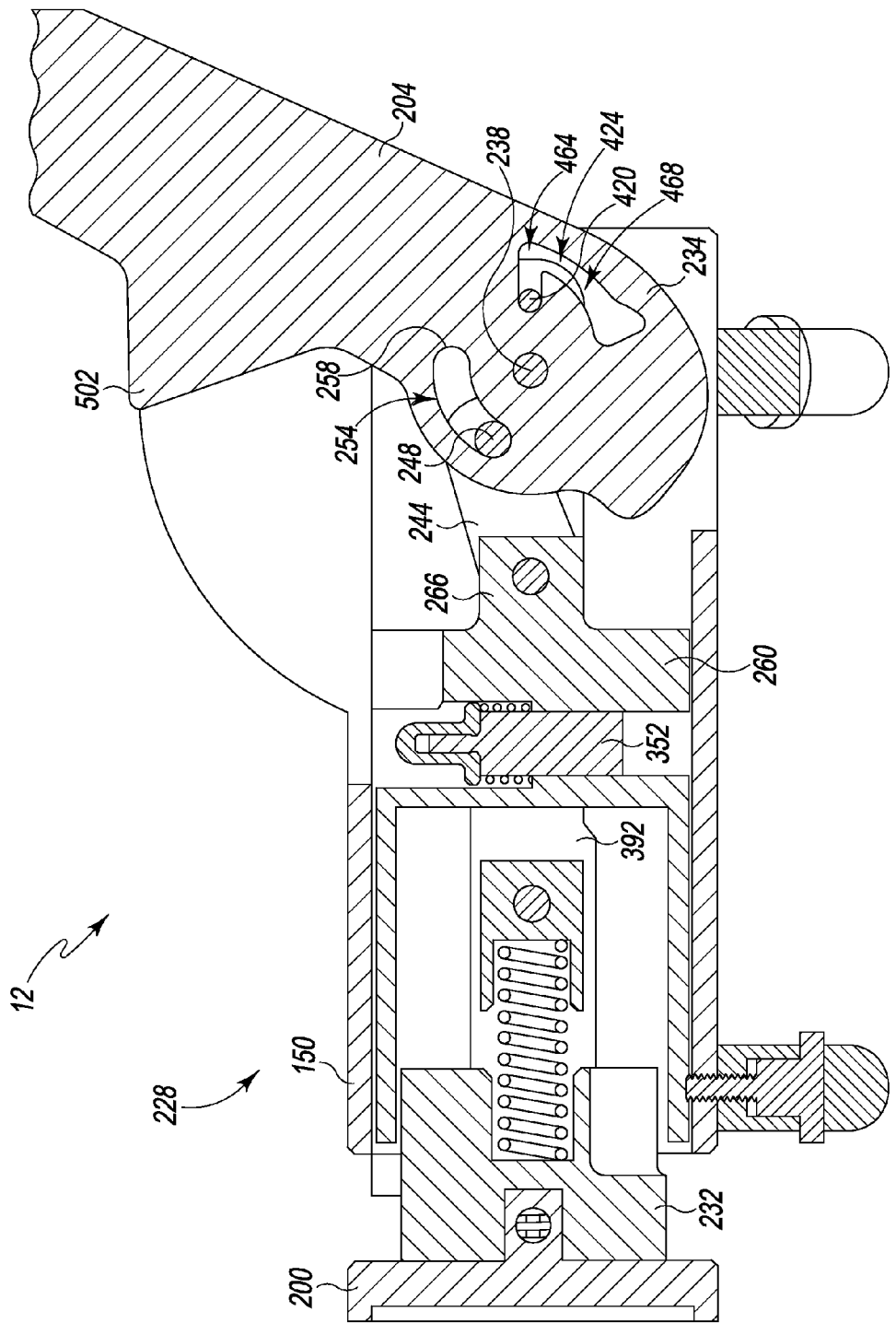
FIGS. 10-13 are cross sectional side elevation views showing various positions of the assembly tool of FIG. 9 as the handle is moved between the raised position and the lowered position.

As described above, the handle 204 of the mechanical actuator 72 is operable to move the ram 200 relative to the housing 150 along an axis 208 to assemble the prosthetic components 10 such as, for example, the femoral component 14 and the stem component 16 shown in FIG. 9. In use, the handle 204 is initially positioned in a raised position relative actuator housing 150. As shown in FIG. 10, when the handle 204 is in the raised position, the notch 464 of the track 424 extends horizontally, and the locking pin 420 is positioned in the notch 464. As a result, rotation of the handle 204 is prevented about the center pin 238.

Returning to FIG. 9, a femoral component 14 may be selected and attached to the holding plate 76 including the appropriate mounting bracket 174 or mounting bracket 176. A stem component 16 also may be selected, and the operator may position the tapered post 30 of the stem component 16 in the tapered bore 48 of the femoral component 14. In doing so, the components 14, 16 are attached but may be decoupled by hand. To secure the components 14, 16 together for implantation, a compressive load must be applied to the components 14, 16 to create a taper lock between the tapered post 30 of the stem component 16 in the tapered bore 48 of the femoral component 14.

The holding plate 76 may then be attached to the frame 70 with the femoral component 14 and the stem component 16. To do so, the holding plate 76 is positioned above the support beam 88 of the frame 70 such that the channels 164 are aligned with the inner shafts 92 of the frame 70. The holding plate 76 may then be moved downward to advance each mounting arm 162 into the slot 158 defined between each inner shaft 92 and each post 156 of the frame 70. Concurrently, the end 68 of the stem component 16 may be advanced through the notch 216 of the ram 200, depending on the position of the telescopic rods 80 of the frame 70. When the closed end 166 of the channel 164 engages the upper surface 108 of the inner shaft 92, the holding plate 76 is properly positioned on the frame 70.

The end 68 of the stem component 16 may be spaced apart from the front surface 214 of the ram 200. To advance the end 68 into contact with the ram 200, the operator may toggle the user-operated buttons 98 to move the locking plates 102 to their respective unlocked positions, thereby permitting the inner shaft 92 to move relative to the outer shaft 90. The operator may then grasp the support beam 88 and advance the holding plate 76 (and hence the components 14, 16) along the axis 208 toward the ram 200. When the end 68 of the stem component 16 is engaged with the ram 200, the ram 200 is moved in the direction indicated by arrow 490 (i.e., toward the housing 150).

Figure 11:
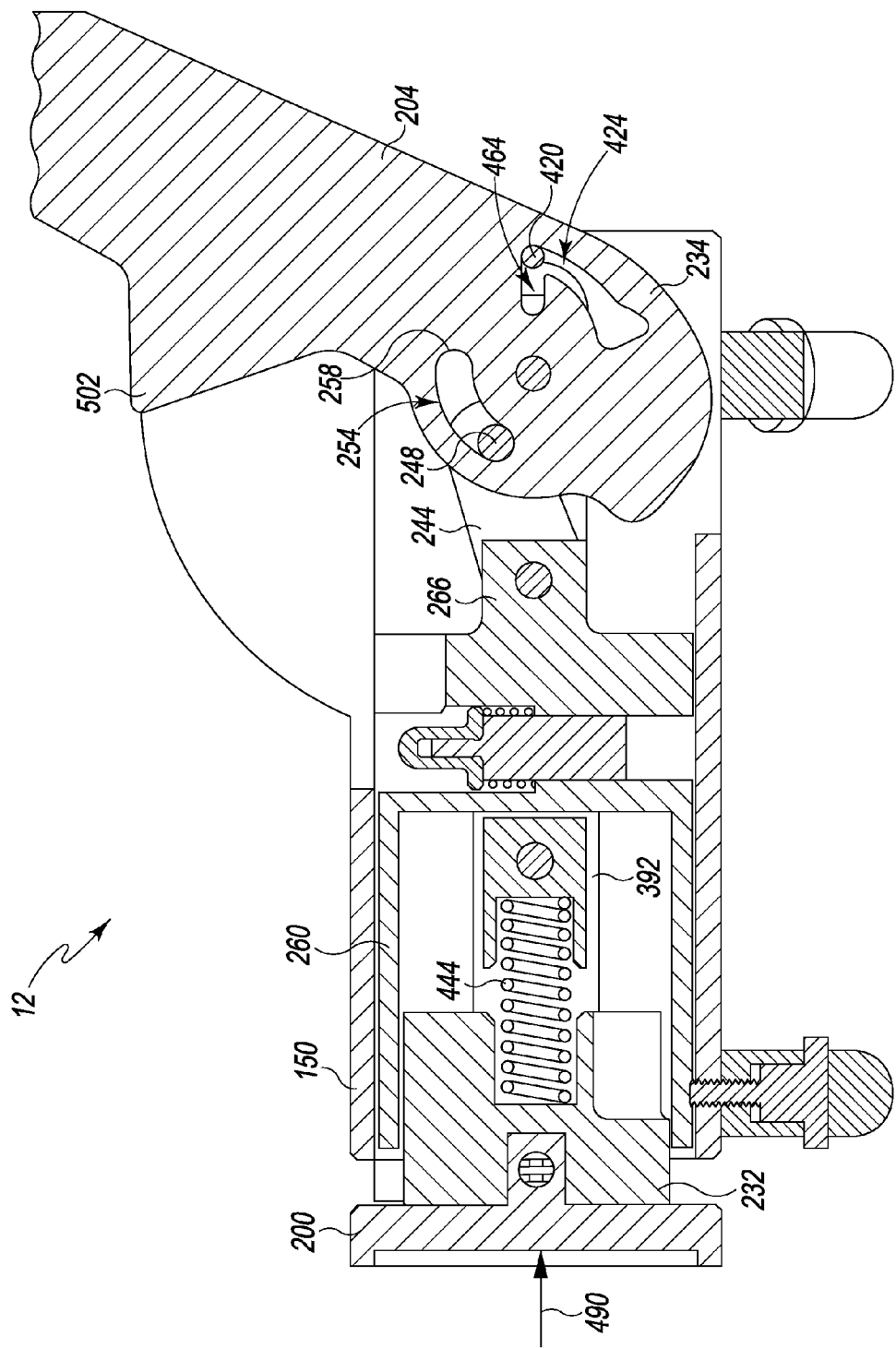

As shown in FIG. 11, the movement of the ram 200 causes the connecting rod 232 to move deeper into the housing 150. In the illustrative embodiment, the bias exerted by the spring 444 is sufficient to cause the link 392 to move with the connecting rod 232. In other embodiments, the cylindrical pin 434 coupling the connecting rod 232 to the link 392 may be moved to the end 442 of the elongated slot 438 such that the link 392 may be moved with the rod 232 and the ram 200. As the link 392 is moved in the direction indicated by arrow 490, the arms 400 of the link 392 slide through the passageways 292 defined in the guide body 260 and the end 402 of the link 392 withdraws the locking pin 420 from the notch 464. The operator may continue to advance the holding plate 76 in the direction indicated by arrow 490 until the locking pin 420 engages the handle base 234 at the back of the curved slot 468, as shown in FIG. 11.

When the locking pin 420 is removed from the notch 464, the handle 204 may be rotated downward toward the housing 150 to move the ram 200 toward the holding plate 76. To do so, the operator may grasp the grip 492 (see FIG. 9) of the handle 204 and apply a force as indicated by arrow 494 in FIG. 11. As the handle 204 is rotated, the cylindrical pin 248 connecting the handle 204 to the link arms 244 is advanced along the track 254 to the upper end 258. When the pin 248 is engaged with the handle base 234 at the upper end 258, further rotation of the handle 204 causes the link arms 244 (and hence the guide body 260) to move in the direction in indicated by arrow 500. Concurrently, the locking pin 420 is advanced along the slot 468 toward the lower end 462 of the track 424. The curved geometry of the slot 468 causes the link 392 to move in the direction in indicated by arrow 500 relative to the connecting rod 232 such that the cylindrical pin 434 is moved to the middle of the elongated slot 438, as shown in FIG. 12.

The movement of the guide body 260 and the link 392 aligns the cross beam 364 of the clutch pin 352 with the grooves 338, 412 defined in the arms 326, 400 of the connecting rod 232 and the link 392, respectively. When the cross beam 364 is aligned with the grooves 338, 412, the spring 356 urges the clutch pin 352 upwardly along the axis 302 such that the cross beam 364 is advanced into the grooves 338, 412. As shown in FIG. 12, the engagement between the connecting rod 232 and the cross beam 364 couples the connecting rod 232 (and hence the ram 200) to the connecting linkage 230 (and hence the handle 204).

When the cross beam 364 is positioned in the grooves 338, 412, further downward rotation of the handle 204 causes the ram 200 to apply a compressive load to the components 14, 16. The load is applied along the axis 208 in the direction indicated by the arrow 500 and is sufficient to create a taper lock between the femoral component 14 and the stem component 16. In the illustrative embodiment, the compressive load is approximately 2700 lbs-force. The total stroke of the ram 200 is between approximately 2 millimeters and 3 millimeters. It should be appreciated that in other embodiments the compressive load and the total stroke may vary based on, for example, the dimensions of the tapered components, including, among other things, the taper diameter, taper length, taper surface finish, taper angle, etc.

Figure 12:
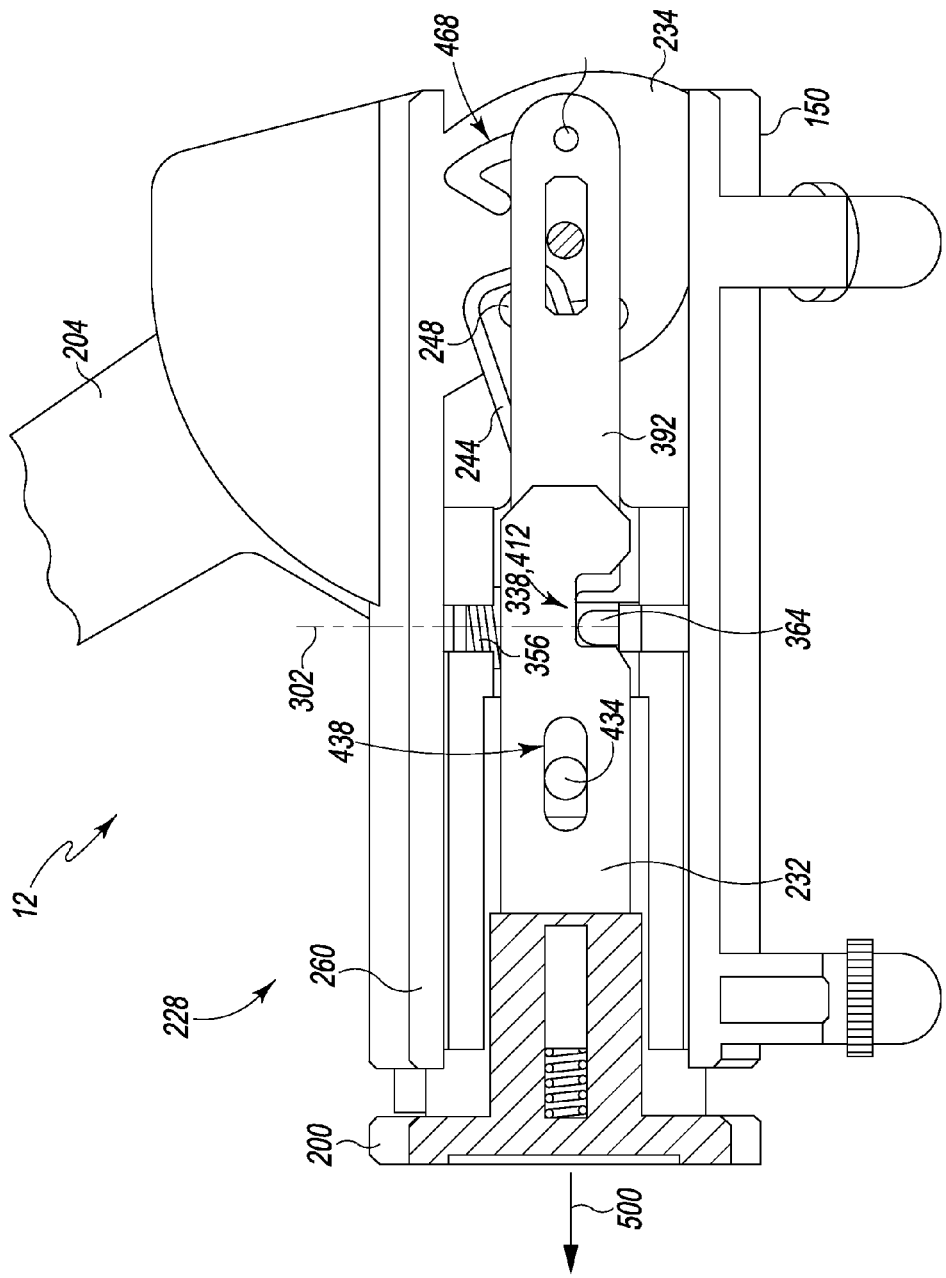
Figure 13:
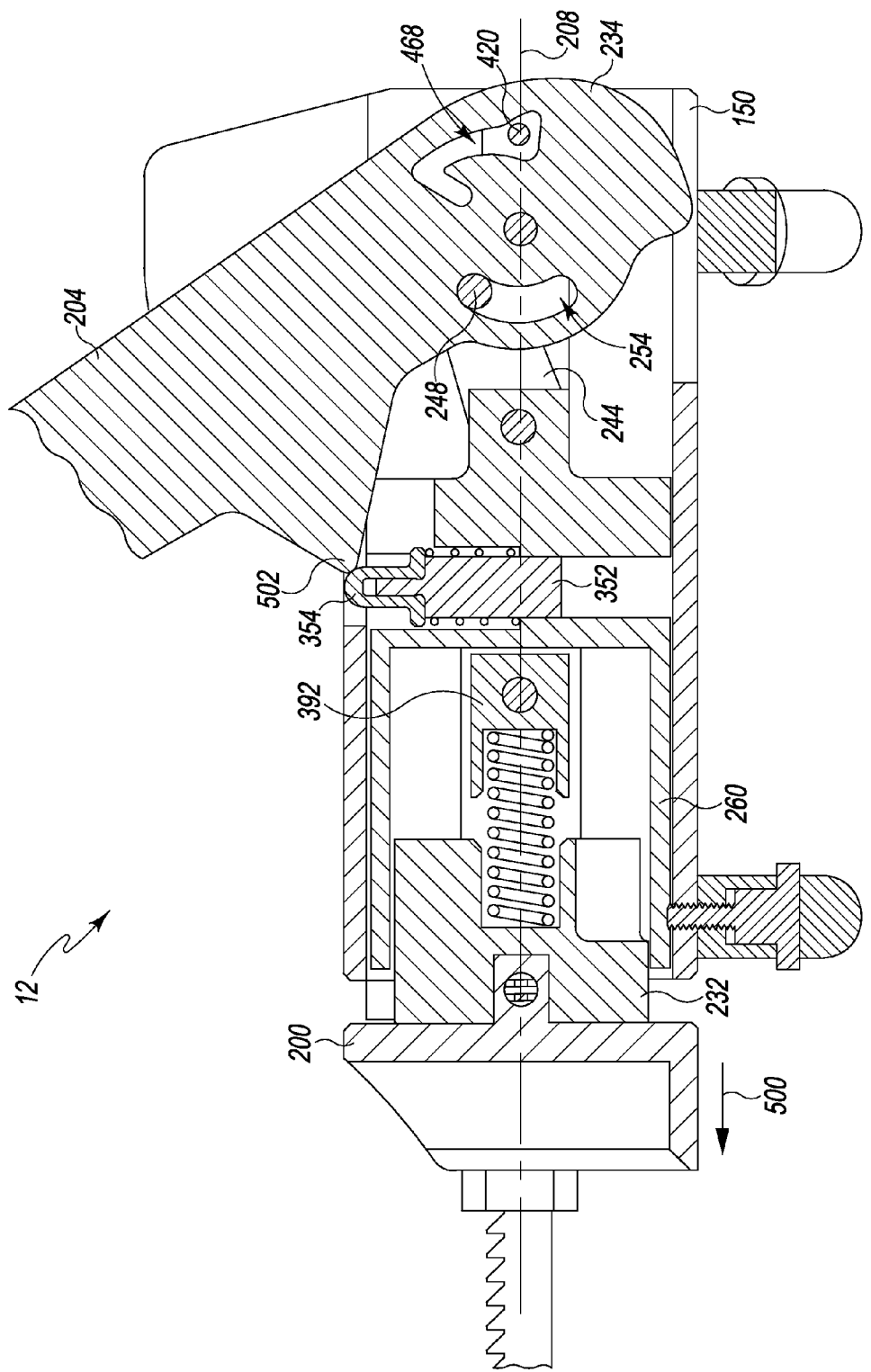

As shown in FIGS. 10-12, rotation of the handle 204 causes a lower tip 502 of the handle 204 to move along the guide slot 224 defined between the flanges 222 of the actuator housing 150. As the handle 204 nears its lowered position (see FIG. 14), the lower tip 502 is advanced into engagement with the stop cap 354 of the clutch 350. When the handle 204 is then moved to the lowered position, the tip 502 of the handle 204 applies sufficient force to the stop cap 354 to overcome the bias exerted by the spring 356 and move the clutch pin 352 downwardly along the axis 302. The cross beam 364 is thereby disengaged from the grooves 338, 412 of the connecting rod 232 and the link 392, respectively, as shown in FIG. 15. As such, the handle 204 is decoupled from the ram 200 such that additional rotation of the handle 204, if any, will not affect the position of the ram 200.

Figure 14:
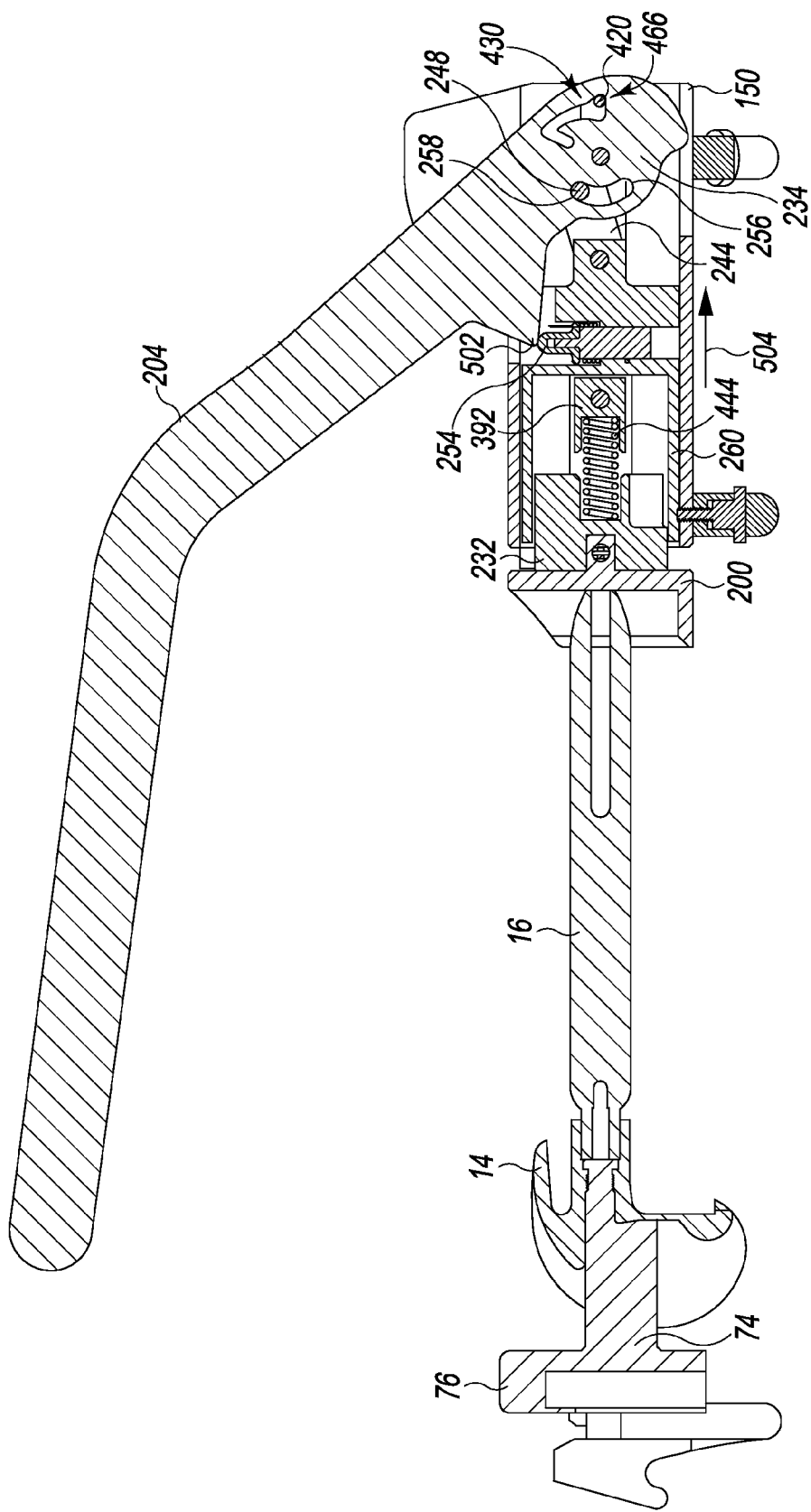
FIG. 14 is a cross sectional side elevation view of the assembly tool of FIG. 9 showing the handle in the lowered position.
Figure 15:
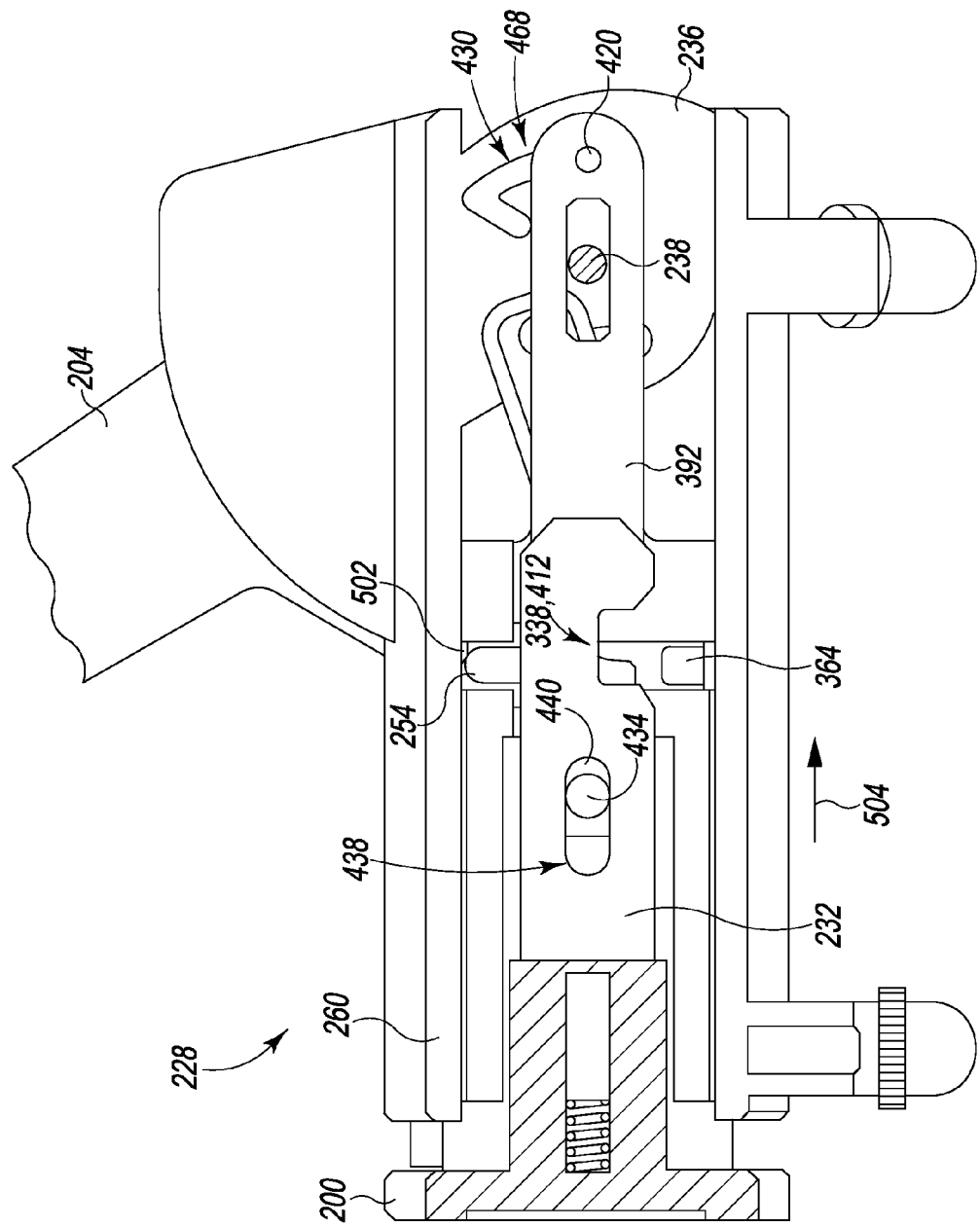
FIG. 15 is another cross sectional side elevation view of the assembly tool in the lowered position.

When the link 392 is disengaged from the clutch pin 352, the bias exerted by the spring 444 urges the link 392 in the direction indicated by arrow 504 in FIG. 14 such that the locking pin 420 is positioned in the pocket 466 of the track 430. The movement of the link 392 causes the grooves 338, 412 of the connecting rod 232 and the link 392 to move out of alignment with each other such that the cross beam 364 is prevented from entering the grooves 338, 412.

To remove the assembled components 14, 16, the operator may return the handle 204 to the raised position. As the handle 204 is rotated upward, the cylindrical pin 248 is moved from the end 258 of the track 254 to the opposite end 256, thereby causing the link arms 244 (and hence the guide body 260) to move in the direction indicated by arrow 504 in FIG. 14. Concurrently, the locking pin 420 is advanced along the slot 468 toward the upper end 460 of the track 424, thereby causing the link 392 to move further in the direction indicated by arrow 504.

As the link 392 is moved with the handle 204, the cylindrical pin 434 coupling the connecting rod 232 to the link 392 returned to the end 440 of the elongated slot 438, thereby causing the connecting rod 232 and the ram 200 to move with the link 392 in the direction indicated by arrow 504. The movement of the ram 200 disengages the ram 200 from the component 16 such that a user may remove the assembled components 14, 16.

When the handle 204 is returned to the raised position, the springs 472 urge the ram 200 (and hence the connecting rod 232) away from the end 284 of the housing 150. When the connecting rod 232 and the ram 200 are moved away from the end 284 of the housing 150, the link 392 is pulled forward via the joint 432 such that the locking pin 420 is advanced into the notch 464, thereby locking the handle 204 in the raised position.

It should be appreciated that a similar procedure may be followed to secure a stem component 16 to a tibial tray 18, a sleeve component 50 to a femoral component 14, or any other combination of prosthetic components 10. To move the handle to the lowered position without loading prosthetic components, an operator may move the ram 200 toward the housing 150 to withdraw the locking pin 420 from the notch 464 and permit the handle 204 to rotate relative to the housing 150. Additionally, in other embodiments, the ram and the support beam 88 may be reversed such that the stem component engages the support beam 88 and the other prosthetic component, e.g., the femoral component, tibial tray, femoral sleeve, etc., engages the ram.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An assembly tool for use in assembling orthopaedic prosthetic components, comprising:
   a frame including a pair of telescopic rods,
   a base plate secured to the telescopic rods, the base plate including a mounting bracket configured to engage a first orthopaedic prosthetic component, and a mechanical actuator including (i) a housing secured to the frame, (ii) a ram plate configured to engage a second orthopaedic prosthetic component, and (iii) a drive mechanism coupled to the ram plate, such that the mechanical actuator is configured to apply a compressive load to the first orthopaedic prosthetic component and the orthopaedic second prosthetic component, wherein the drive mechanism includes:

a connecting rod coupled to the ram plate, a handle rotatively coupled to the housing, and a clutch pin that is moveable between (i) an engaged position in which the handle is coupled to the connecting rod such that rotation of the handle causes the ram plate to move toward the base plate and (ii) a disengaged position in which the handle is decoupled from the connecting rod such that the ram plate remains stationary when the handle is rotated, wherein when the handle is rotated from a first position to a second position, the handle engages an end of the clutch pin to move the clutch pin from the engaged position to the disengaged position.

2. The assembly tool of claim 1, wherein:

each telescopic rod includes a first shaft moveably coupled to a second shaft, the first shaft including a plurality of teeth, and the frame includes a locking plate including a plurality of teeth configured to engage the teeth of the first shaft, the locking plate being moveable between (i) a locked position in which the teeth of the locking plate are interdigitated with the teeth of the first shaft to prevent the first shaft from moving relative to the second shaft and (ii) an unlocked position in which the teeth of the locking plate are spaced apart from the teeth of the first shaft such that the first shaft is permitted to move relative to the second shaft.

3. The assembly tool of claim 1, wherein the housing of the mechanical actuator is removably coupled to the frame.

4. The assembly tool of claim 1, wherein:

the ram plate is configured to move along a first axis toward the base plate when the handle is rotated, and the clutch pin is configured to move along a second axis between the engaged position and the disengaged position, the second axis extending orthogonal to the first axis.

5. The assembly tool of claim 4, wherein the connecting rod has a slot defined therein, and the clutch pin includes a cross beam that is (i) received in the slot when the clutch pin is in the engaged position and (ii) spaced apart from the slot when the clutch pin is in the disengaged position.

6. The assembly tool of claim 5, wherein:

the drive mechanism further includes (i) a guide body positioned in the housing, the guide body including an aperture extending along the first axis and a guide slot extending along the second axis, and (ii) a link arm connecting the guide body and the handle, and a connecting rod extends outwardly from the aperture to an end coupled to the ram plate and the cross beam of the clutch pin is moveable along the guide slot between the engaged position and the disengaged position.

7. The assembly tool of claim 6, wherein the link arm is coupled to the handle via a joint, the joint including (i) a curved track defined in the handle and (ii) a cylindrical pin positioned in the curved track, the cylindrical pin being configured to move along the curved track when the handle is moved between the first position and the second position.

8. The assembly tool of claim 5, further comprising a locking mechanism coupled to the connecting rod, the locking mechanism being configured to prevent rotation of the handle.

9. The assembly tool of claim 8, wherein:

the locking mechanism includes (i) a link having a first end moveably coupled to the connecting rod, and (ii) a pin secured to a second end of the link, and the link is moveable between (i) a locked position in which the pin is received in a notch defined in the handle such that rotation of the handle is prevented, and (ii) an unlocked position in which the pin is spaced apart from the notch such that rotation of the handle is permitted.

10. The assembly tool of claim 9, wherein the link has a slot defined therein and the cross beam of the clutch pin is (i) received in the slot of the link when the clutch pin is in the engaged position and (ii) spaced apart from the slot of the link when the clutch pin is in the disengaged position.

11. The assembly tool of claim 9, wherein the link is moved to the unlocked position when a predetermined amount of force is applied to the ram plate in a direction away from the base plate.

12. An assembly tool for use in assembling orthopaedic prosthetic components, comprising:

a frame, a base plate coupled to the frame, the base plate including a mounting bracket configured to engage a first orthopaedic prosthetic component, and a mechanical actuator including (i) a housing secured to the frame, (ii) a ram plate configured to engage a second orthopaedic prosthetic component, and (iii) a drive mechanism coupled to the ram plate, such that the mechanical actuator is configured to apply a compressive load to the first orthopaedic prosthetic component and the orthopaedic second prosthetic component, wherein the drive mechanism includes:

a handle rotatively coupled to the housing, the handle being operable to move the ram plate toward the base plate, and a locking mechanism configured to prevent rotation of the handle, the locking mechanism including a linkage coupled to the ram plate and a pin, the linkage being moveable between (i) a locked position in which the pin is received in a notch defined in the handle such that rotation of the handle is prevented, and (ii) an unlocked position in which the pin is spaced apart from the notch such that rotation of the handle is permitted, wherein the linkage is moved to the unlocked position when a predetermined amount of force is applied to the ram plate in a direction away from the base plate.

13. The assembly tool of claim 12, wherein the drive mechanism further includes:

a clutch pin that is moveable between (i) an engaged position in which the handle is coupled to the ram plate such that rotation of the handle causes the ram plate to move toward the base plate and (ii) a disengaged position in which the handle is decoupled from the ram plate such that the ram plate remains stationary when the handle is rotated, wherein the handle is configured to engage the clutch pin during rotation to move the clutch pin from the engaged position to the disengaged position.

14. The assembly tool of claim 13, wherein the linkage has a slot defined therein, and the clutch pin includes a cross beam that is (i) received in the slot of the linkage when the clutch pin is in the engaged position and (ii) spaced apart from the slot of the linkage when the clutch pin is in the disengaged position.

15. The assembly tool of claim 13, wherein the clutch pin is biased in the engaged position.

16. The assembly tool of claim 12, further comprising a plurality of base plates configured to be coupled to the frame, each base plate including a mounting bracket configured to engage a different orthopaedic prosthetic component.

* * * * *